(12) United States Patent
Zhong et al.

(10) Patent No.: US 11,013,518 B2
(45) Date of Patent: May 25, 2021

(54) DETACHABLE ENDOSCOPIC CLIP FOR ANASTOMOSIS

(71) Applicant: NINGBO SENSCURE BIOTECHNOLOGY CO., LTD., Zhejiang (CN)

(72) Inventors: Hao Zhong, Zhejiang (CN); Zhimin Chen, Zhejiang (CN); Shiwen Lv, Zhejiang (CN)

(73) Assignee: NINGBO SENSCURE BIOTECHNOLOGY CO., LTD., Ningbo (CN)

( * ) Notice: Subject to any disclaimer, the term of this patent is extended or adjusted under 35 U.S.C. 154(b) by 0 days.

(21) Appl. No.: 17/087,820

(22) Filed: Nov. 3, 2020

(65) Prior Publication Data

US 2021/0045747 A1    Feb. 18, 2021

Related U.S. Application Data

(63) Continuation of application No. PCT/CN2019/091112, filed on Jun. 13, 2019.

(30) Foreign Application Priority Data

Jun. 14, 2018  (CN) .......................... 201810614849.6

(51) Int. Cl.
*A61B 17/122* (2006.01)
*A61B 17/00* (2006.01)
*A61B 17/12* (2006.01)

(52) U.S. Cl.
CPC ............... *A61B 17/1227* (2013.01); *A61B 2017/00862* (2013.01); *A61B 2017/12004* (2013.01)

(58) Field of Classification Search
CPC ....... A61B 17/08; A61B 17/083; A61B 17/12; A61B 17/122; A61B 17/1227; A61B 2017/081; A61B 2017/12004
See application file for complete search history.

(56) References Cited

U.S. PATENT DOCUMENTS

| | | | | |
|---|---|---|---|---|
| 5,312,426 | A | * | 5/1994 | Segawa .............. A61B 17/1227 24/545 |
| 5,868,763 | A | * | 2/1999 | Spence .................. A61B 17/11 606/139 |
| 6,210,419 | B1 | * | 4/2001 | Mayenberger ....... A61B 17/122 606/120 |
| 6,428,548 | B1 | * | 8/2002 | Durgin .................. A61B 17/10 606/142 |

(Continued)

FOREIGN PATENT DOCUMENTS

| | | |
|---|---|---|
| CN | 205658947 U | 10/2016 |
| CN | 107374691 A | 11/2017 |

(Continued)

*Primary Examiner* — Ryan J. Severson

(57) ABSTRACT

Provided is a detachable endoscopic clamp, related to medical apparatuses, which aims to solve the problem that the existing endoscopic clips are hard to remove and can only provide a weak clipping force. The detachable endoscopic clip includes at least two engagement members and at least two resilient members. Ends of the engagement members and ends of the resilient members from conjugates, and at least one of the conjugates is detachable. The endoscopic clip can be easily detached and removed after a surgery.

10 Claims, 22 Drawing Sheets

(56) References Cited

U.S. PATENT DOCUMENTS

| | | | |
|---|---|---|---|
| 6,849,078 B2* | 2/2005 | Durgin | A61B 17/10 606/142 |
| 6,911,032 B2* | 6/2005 | Jugenheimer | A61B 17/122 600/104 |
| 7,488,334 B2* | 2/2009 | Jugenheimer | A61B 17/122 606/142 |
| 7,892,244 B2* | 2/2011 | Monassevitch | A61B 17/0643 606/151 |
| 8,043,307 B2* | 10/2011 | Jugenheimer | A61B 17/122 606/142 |
| 8,187,286 B2* | 5/2012 | Jugenheimer | A61B 17/1285 606/142 |
| 8,192,349 B2* | 6/2012 | Schurr | A61B 17/083 600/37 |
| 8,663,245 B2* | 3/2014 | Francischelli | A61B 17/12013 606/142 |
| 8,685,043 B2* | 4/2014 | Jugenheimer | A61B 17/10 606/142 |
| 8,784,436 B2* | 7/2014 | Ho | A61B 17/083 606/142 |
| 9,017,349 B2* | 4/2015 | Privitera | A61B 17/1285 606/157 |
| 9,149,265 B2* | 10/2015 | Ehrenreich | A61B 17/0206 |
| 9,370,369 B2* | 6/2016 | Size | A61B 17/1227 |
| 9,468,431 B2* | 10/2016 | Ehrenreich | A61B 17/0206 |
| 9,901,351 B2* | 2/2018 | Winkler | A61B 17/1227 |
| 9,955,960 B2* | 5/2018 | Ehrenreich | A61B 1/32 |
| 10,166,024 B2* | 1/2019 | Williamson, IV | A61B 17/083 |
| 2002/0032454 A1* | 3/2002 | Durgin | A61B 17/10 606/151 |
| 2002/0055750 A1* | 5/2002 | Durgin | A61B 17/10 606/151 |
| 2002/0062130 A1 | 5/2002 | Jugenheimer et al. | |
| 2003/0153932 A1* | 8/2003 | Spence | A61B 17/11 606/153 |
| 2004/0097982 A1* | 5/2004 | Jugenheimer | A61B 17/1227 606/151 |
| 2006/0100649 A1* | 5/2006 | Hart | A61B 17/08 606/157 |
| 2006/0264984 A1 | 11/2006 | Schurr et al. | |
| 2007/0112365 A1* | 5/2007 | Hilal | A61B 17/122 606/157 |
| 2007/0213747 A1* | 9/2007 | Monassevitch | A61B 17/0643 606/151 |
| 2011/0046437 A1* | 2/2011 | Kassab | A61F 5/0086 600/37 |
| 2011/0046641 A1* | 2/2011 | Kassab | A61F 5/0086 606/139 |
| 2012/0095480 A1 | 4/2012 | Jugenheimer et al. | |
| 2014/0039271 A1* | 2/2014 | Ehrenreich | A61B 17/0206 600/217 |
| 2014/0142597 A1 | 5/2014 | Winkler et al. | |
| 2014/0228864 A1 | 8/2014 | Jugenheimer et al. | |
| 2014/0343581 A1* | 11/2014 | Lee | A61B 17/10 606/151 |

FOREIGN PATENT DOCUMENTS

| | | |
|---|---|---|
| CN | 109044473 A | 12/2018 |
| CN | 209059324 U | 7/2019 |
| EP | 2449983 A1 | 5/2012 |

\* cited by examiner

DETACHABLE ENDOSCOPIC CLIP FOR ANASTOMOSIS

CROSS-REFERENCE TO RELATED APPLICATIONS

This application is a continuation of International Patent Application No. PCT/CN2019/091112, filed on Jun. 13, 2019, which claims the benefit of priority from Chinese Patent Application No. 201810614849.6, filed on Jun. 14, 2018. The content of the aforementioned applications, including any intervening amendments thereto, is incorporated herein by reference in its entirety.

TECHNICAL FIELD

The present application relates to medical apparatuses, more particularly to a detachable endoscopic clip for anastomosis.

BACKGROUND

Gastrointestinal (GI) bleeding is a common clinical symptom of gastrointestinal tract diseases and is divided into upper gastrointestinal bleeding and lower gastrointestinal bleeding according to sites of bleeding. Arterial bleeding has a high mortality rate, where a mortality rate of an acute artery bleeding of the GI tract is about 10%, and the mortality rate of patients over 60 years old ranges from 30% to 50%, which is higher than that of young patients.

Gastrointestinal perforation is also a common clinical symptom of the gastrointestinal tract diseases. Patients with GI perforation, aged from 30 to 60 years old, roughly account for 75% of the total patients with GI perforation. A mortality rate of GI perforation is about 27%, and the mortality rate increases as the age of the patient increases.

Hemoclips are widely applied in the treatment of gastrointestinal bleeding and gastrointestinal perforation. However, a hemoclip has a small clipping scope and a weak clipping force, so that the hemoclip cannot effectively treat gastrointestinal bleeding and gastrointestinal perforation. Aiming at above-mentioned defects, Over-the-scope Clips (OTSCs) with large clipping scope and strong clipping force are commercially available. Nevertheless, the OTSC is expensive, and is hard to be removed after released. Specifically, a specific electric arc cutting apparatus is needed to cut off the anastomosis clip (i.e., the OTSC), so as to realize the removal.

Generally, the commercially available endoscopic clips for anastomosis are formed integrally, and need to be removed integrally since it cannot be detached. However, it is hard to integrally remove the endoscopic clip, and a second damage may be caused to the tissues, which increases the difficulty to remove the endoscopic anastomosis clips.

SUMMARY

Based on above-mentioned analysis, an object of the present invention is to provide a detachable endoscopic clip for anastomosis to solve the problem that endoscopic clips in the prior art are hard to remove and can only provide a weak clipping force.

The technical solutions of the present application are as follows.

A detachable endoscopic clip comprises at least two engagement members and at least two resilient members. Ends of the at least two engagement members are respectively connected to ends of the at least two resilient members to form a plurality of conjugates; and at least one of the conjugates is detachable.

In some embodiments, each of the plurality of conjugates is assembled through a binding wire, a tube, a pin, a clamp or a combination thereof.

In some embodiments, a limit portion is provided at an end of at least one of the at least two engagement members and an end of at least one of the at least two resilient members respectively, and the limit portion is a limit groove, a pinhole, or a clamping slot.

In some embodiments, each of the conjugates is assembled by a binding wire, where a limit groove is provided at the ends of the at least two engagement members and the ends of the at least two resilient members respectively.

In some embodiments, each of the conjugates is assembled by a tube, where a limit groove is provided at the ends of the at least two engagement members and the ends of the at least two resilient members respectively, and a limit part engaged with the limit groove is provided at the tube.

In some embodiments, each of the conjugates is assembled by a pin, where a pinhole is provided at the ends of the at least two engagement members and the ends of the at least two resilient members respectively, and a pin is insertable into the pinhole to fixedly connect the ends of the at least two engagement members and the ends of the at least two resilient members.

In some embodiments, each of the conjugates is assembled through a clamp, where a clamping slot engaged with the clamp is provided at the ends of the at least two engagement members and the ends of the at least two resilient members respectively.

In some embodiments, each of the conjugates is assembled through the binding wire, the tube, the pin, the clamp or the combination thereof, and the binding wire, the tube, the pin, the clamp or a combination thereof is engaged with the limit part.

In some embodiments, a pulling portion is provided at the binding wire, the tube, the pin or the clamp.

In some embodiments, the at least two engagement members comprise a first engagement member and a second engagement member, and the at least two resilient members comprise a first resilient member and a second resilient member. Ends of the first engagement member, the first resilient member, the second engagement member, and the second resilient member form a plurality of conjugates; the first engagement member and the second engagement member engage with each other when at least one of the conjugates is assembled through a detachable connector; and the first engagement member and the second engagement member are separated from each other when the detachable connector is detached.

In some embodiments, two of the plurality of conjugates that are diagonally opposite to each other are detachable.

In some embodiments, two adjacent conjugates of the plurality of conjugates are detachable.

In some embodiments, at least one of the at least two engagement members and at least one of the at least two resilient members are integrally formed, respectively; each of the at least two engagement members is provided with teeth; and each of the at least two resilient members is a protrusion that is resilient and is arranged at both sides of each of the at least two engagement members.

In some embodiments, the at least two resilient members are made of metal.

In some embodiments, a sharp portion is provided at the teeth.

In some embodiments, the at least two engagement members are made of metal or polymer.

In some embodiments, the at least two resilient members are of an arc structure. In some embodiments, the at least two resilient members are of a torsion-spring structure.

In some embodiments, the binding connection is realized by winding, and an end of the binding wire is fixedly connected to the at least two engagement members or the at least two resilient members.

In some embodiments, the binding connection is realized by tying, and the binding wire is limited in a limit groove.

In some embodiments, the binding wire is made of metal or polymer.

In some embodiments, a pinhole is provided at the ends of the at least two the engagement members and the ends of the at least two resilient members, and a through hole engaged with the pinhole is provided at a tube. A pin is insertable into the through hole and the pinhole to fix the tube.

In some embodiments, a limit groove is provided at the ends of the at least two engagement members and the ends of the at least two resilient members respectively, and an opening corresponding to the limit groove is provided at a side wall of a tube. The limit groove and the opening are bound by the binding wire to fix the tube.

In some embodiments, there are two engagement members and two resilient members which are independent from each other. The two engagement members and the two resilient members are connected to form the endoscopic clip with four detachable conjugates.

In some embodiments, two engagement members and two resilient members are provided, and a first engagement member and a first resilient member are fixedly connected to be an independent structure, and the independent structure, a second engagement member and a second resilient member are connected to form the endoscopic clip with three conjugates which are detachable.

In some embodiments, two engagement members and two resilient members are provided, and a first engagement member and a first resilient member are fixedly connected to be an independent structure, whereas a second engagement member and a second resilient member are fixedly connected to be another independent structure, and two independent structures are connected to form the endoscopic clip with two diagonally opposite conjugates which are detachable.

In some embodiments, two engagement members and two resilient members are provided, and a first resilient member and a second resilient member are respectively fixedly connected to two ends of a first engagement member to be an independent structure, and the independent structure and a second engagement member are connected to form the endoscopic clip with two adjacent conjugates which are detachable.

In some embodiments, two engagement members and two resilient members are provided. A curvity of a first resilient member is larger than that of a second resilient member. An end of a first engagement member and an end of a second engagement member are respectively fixedly connected to two ends of the first resilient member, and an end of the second resilient member is fixedly connected to the other end of the second engagement member, and the other end of the second resilient member is connectable to the other end of the first engagement member.

In some embodiments, at least three engagement members are provided, and the engagement members are fixedly connected with the resilient member. The ends of the engagement members are connected to form a plurality of detachable conjugates.

In some embodiments, the endoscopic clip is mounted outside a transparent cap of an endoscope.

In some embodiments, the endoscopic clip is releasable by pulling the pulling portion.

Compared with the prior art, the beneficial effects of the present invention are described as follows.

a) The engagement members and the resilient members are connected to form the endoscopic clip with detachable conjugates. The endoscopic clip has a simple structure, in which the endoscopic clip is disassembled by detaching the conjugates. The endoscopic clip does not have to be integrally removed, whereas it can be disassembled first and then be removed, so endoscopic clip can be easily removed. Especially, when the teeth of the endoscopic clip are covered by a tissue, the endoscopic clip can be removed through pulling out the members of the detached endoscopic clip from the covering tissue, which reduces damage to the surrounding tissues when removing the endoscopic clip.

b) The resilient members are made of metal and can provide the endoscopic clip with a stable and strong clipping force. The engagement members, made of metal or polymer, have good biomechanical performance and corrosion resistance, which extends the service life of the endoscopic clip. The teeth of the engagement members are provided with sharp portions. When the endoscopic clip is released, the engagement members are closed and the sharp portions stick into the tissue, so that the endoscopic clip can clasp the tissue tightly and give an excellent closing performance.

c) The detachable conjugates can be oppositely, adjacently or centrally arranged. The positions of the detachable conjugates are not fixed, which allows doctors to operate more easily in a limited endoscopic vision.

The above-mentioned technical solutions of the present application are combinable with each other. The features and advantages of the present application will be further described in the following description.

BRIEF DESCRIPTION OF THE DRAWINGS

The accompany drawing disclosed herein are merely illustrative and not intend to limit the scope of the present application. In the drawings, the same numerals represent the same parts.

Figure 1:
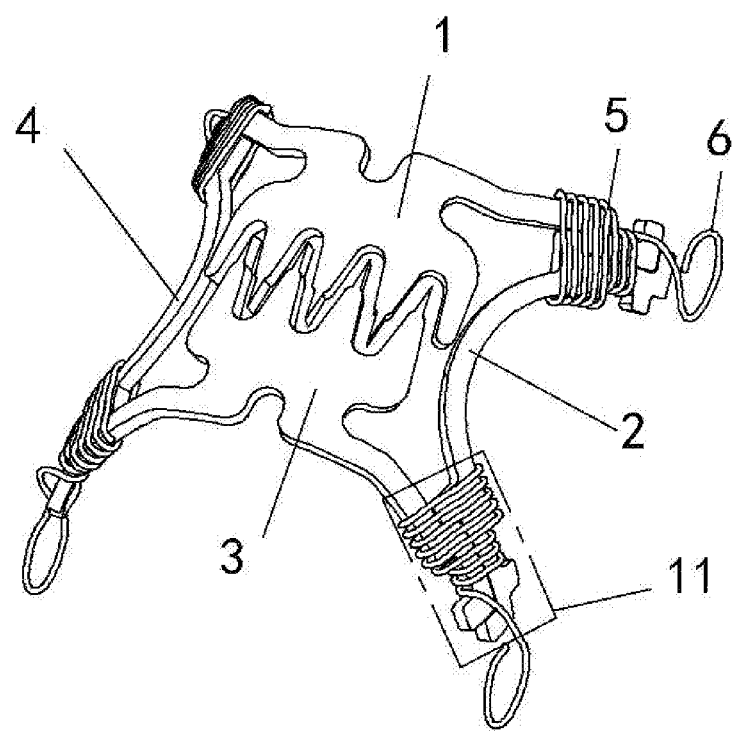
FIG. 1 is a schematic diagram of an endoscopic clip according to a first embodiment of the present application.
Figure 2:
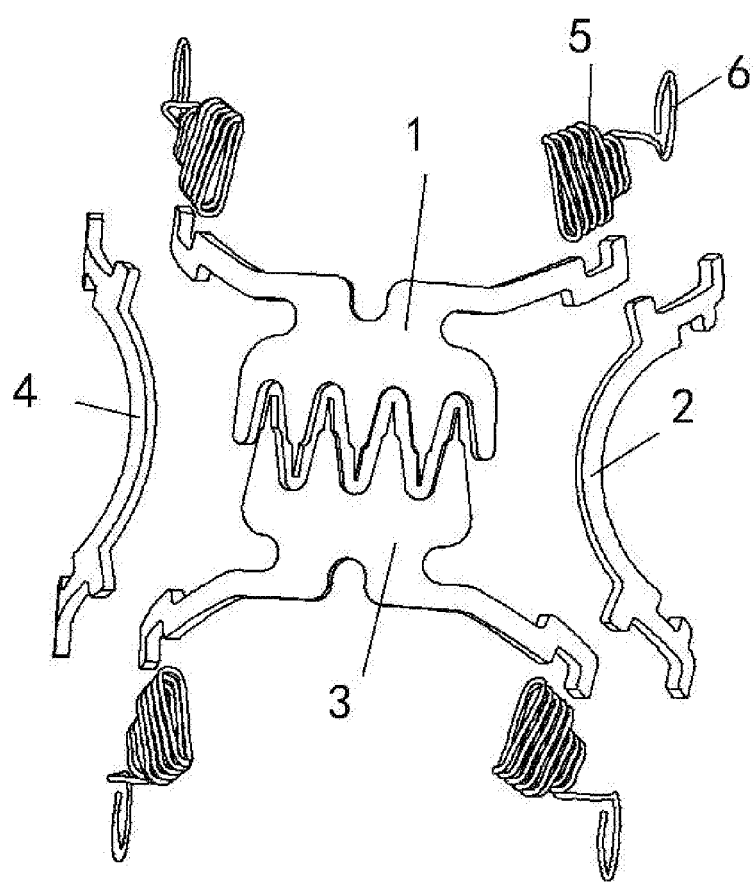
FIG. 2 is a schematic diagram of the endoscopic clip in FIG. 1, in which the endoscopic clip is being detached.
Figure 3:
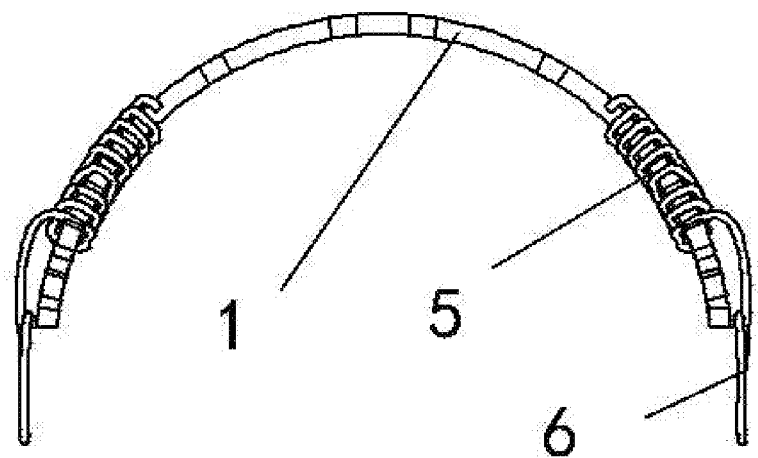
FIG. 3 is a front view of the endoscopic clip in FIG. 1.
Figure 4:
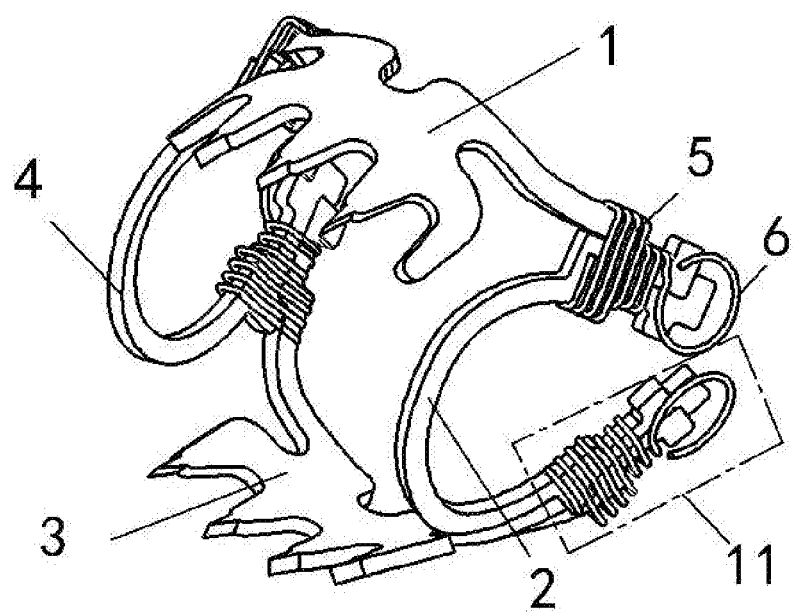
FIG. 4 is a schematic diagram of the endoscopic clip in FIG. 1 in an open state.
Figure 5:
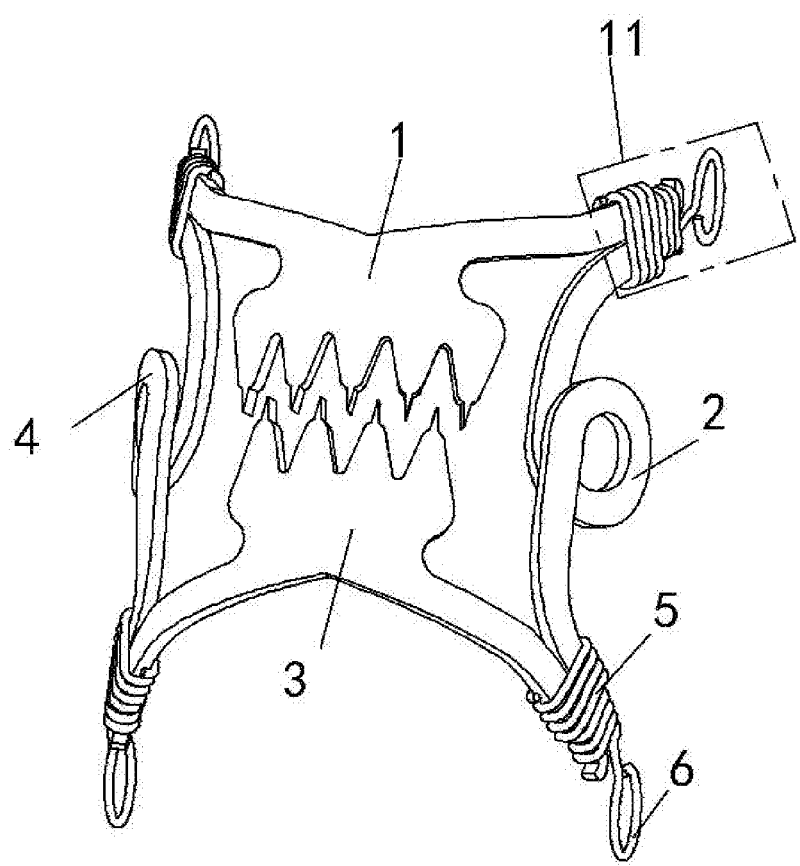
FIG. 5 is a schematic diagram of the endoscopic clip according to the first embodiment of the present application, in which a resilient member is a torsion spring.

In the drawings, 1, first engagement member; 2, first resilient member; 3, second engagement member; 4, second engagement member; 5, binding wire; 6, pulling portion; 7, tube; 8, pin; 9, transparent cap; 10, pulling wire; 11, conjugate; 12, clamp.

DETAILED DESCRIPTION OF EMBODIMENTS

Preferred embodiments are described with reference to accompany drawings. It should be noted that the accompany drawings disclosed herein are merely illustrative and not intend to limit the scope of the present application.

Embodiment 1

A first embodiment of a detachable endoscopic clip for anastomosis of the present application is illustrated in FIGS. 1-11. As shown in FIGS. 1-5, the detachable endoscopic clip includes a first engagement member 1, a first resilient member 2, a second engagement member 3, and a second resilient member 4. The first engagement member 1 and the second engagement member 3 are both provided with teeth and protrusions. Ends of the first engagement member 1, the first resilient member 2, the second engagement member 3, and the second resilient member 4 form four conjugates 11 which are detachable through detachable connectors. The first engagement member 1 and the second engagement member 3 engage with each other when the conjugates 11 are assembled, and the first engagement member 1 and the second engagement member 3 are separated from each other when the conjugates 11 are detached. The detachable connector is a binding wire 5, that is, the conjugate 11 is assembled by connecting the protrusion of the resilient member and the engagement member through the binding wire 5. Each end of the two engagement members and the two resilient members is provided with a limit portion to limit locations of the engagement members, the resilient members, and the binding wire 5. The limit portion is a limit groove. The binding wire 5 is made of metal or polymer. The conjugate 11 is assembled by winding the binding wire 5, while the conjugate 11 is detachable by reverse winding of the binding wire 5.

The binding wire 5 is preferably made of stainless strain to give a better binding performance, where the stainless steel wire is capable of maintaining a wound shape, so that the stainless steel wire can fasten the conjugate 11 without knotting, which is convenient to operate and has a good fixing performance. The binding wire 5 is wound without overlap to avoid knotting of itself during the detachment, which allows the detachable endoscopic clip to be rapidly removed.

In order to facilitate the removal of the detachable endoscopic clip, an end of the binding wire 5 is connected to one of the engagement members or one of the resilient members, so that when the endoscopic clip is detached, the binding wire is still in connection with the engagement member or the resilient member.

In order to facilitate the removal of the endoscopic clip, the other end of the binding wire 5 is provided with a circular pulling portion 6. To realize the detachment of the detachable endoscopic clip, a detaching member is inserted into the circular pulling portion 6 and then is wound in the reverse winding direction of the binding wire 5 to untie the binding wire 5.

The first resilient member 2 and the second resilient member 4 are made of metals with resilience, such as spring steel, which can provide a large clipping force. In some embodiments, the first resilient member 2 and the second resilient member 4 are made of nickel-titanium shape-memory alloy, so that the resilient members can return to their pre-deformed shape under an operating temperature to provide a stable clipping force. The first resilient member 2 and the second resilient member 4 are of an elongated shape, and preferably an arc shape. In some embodiments, the resilient members can be a torsion spring shown in FIG. 5. The endoscopic clip is of an arc structure when the conjugates 11 are assembled. The teeth are covered by the tissue when the detachable endoscopic clip is released, while the conjugates 11 are exposed outside the tissue, so as to render the removal of the detachable endoscopic clip convenient.

In order to ensure a good engagement performance, the engagement member is made of metal with excellent resilience, such as spring steel. nickel-titanium alloy, and the engagement member can also be made of resilient polymer, such as polyformaldehyde. The engagement member is of a rake shape or a needle shape, and the teeth are provided with sharp portions. When the endoscopic clip is released, the engagement members are closed and the sharp portions stick into the tissue, so that the endoscopic clip can clasp the tissue tightly, which has an excellent closing performance.

Figure 6:
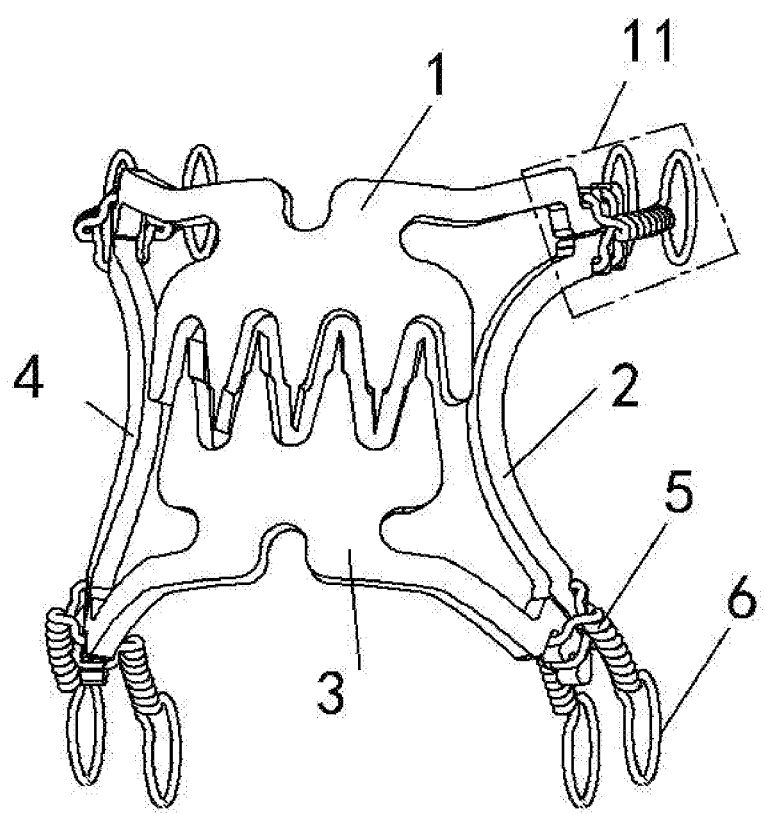
FIG. 6 is a schematic diagram of the endoscopic clip according to the first embodiment of the present application, in which the resilient member and the engagement member are bond through a binding wire.

In some embodiments, the binding connection may be realized by tying. As shown in FIG. 6, the binding wire is provided at the limit groove to fasten the end of the engagement member and the end of the resilient member. Then the conjugate 11 is detachable by reverse twisting of the binding wire to detach and remove the endoscopic clip from the tissue. The binding wire is made of hard material, and preferably metal, for the metal wire is easy to be fastened tightly. Two ends of the binding wire can be provided with circular pulling portion to make the untying and removal of the binding wire more easily.

Figure 7:
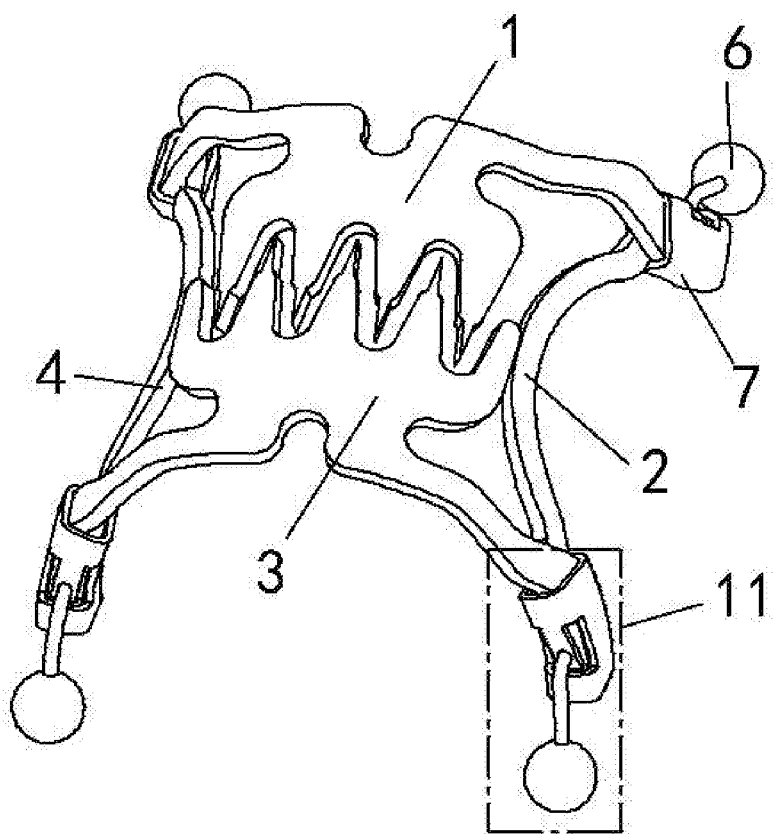
FIG. 7 is a schematic diagram of the endoscopic clip according to the first embodiment of the present application, in which the resilient member and an engagement member are connected through a tube.

In some embodiments, the conjugate 11 can be assembled through a tube. As shown in FIG. 7, a limit groove is provided at each end of the first engagement member 1, the second engagement member 3, the first resilient member 2 and the second resilient member 4. A limit part engaged with the limit groove is provided at the tube 7, so that the first engagement member and the second engagement member are respectively connected to the first resilient member and the second resilient member through tubes. A spherical pulling portion 6 is provided at the tube 7. The endoscopic clip is easily detachable through detaching the tube 7. The tube 7 is made of hard material, and preferably metal, for the metal tube with little distortion has a stiffer structure, a better fastening performance and a longer service life.

Figure 8:
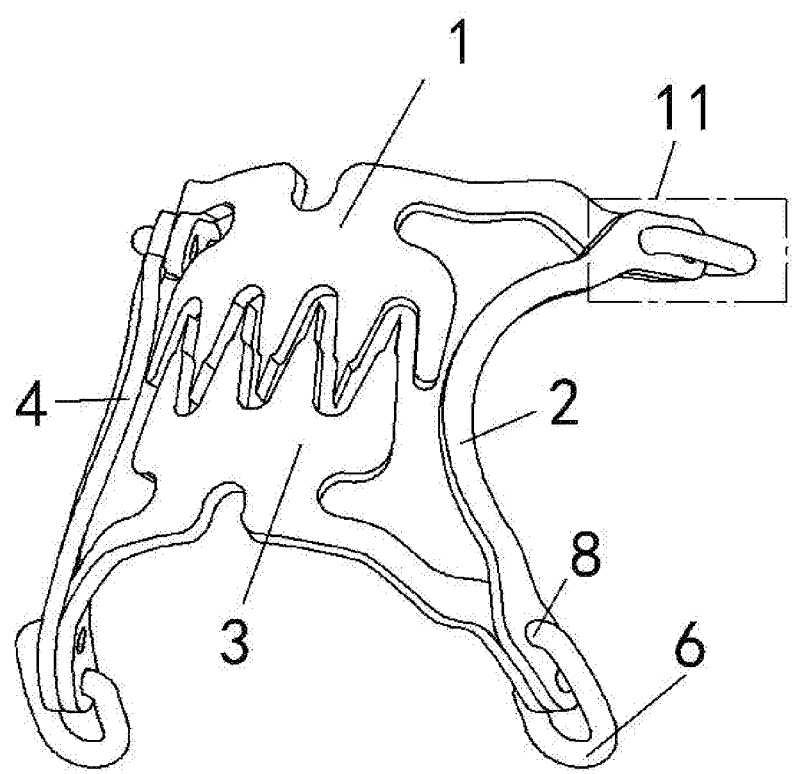
FIG. 8 is a schematic diagram of the endoscopic clip according to the first embodiment of the present application, in which the resilient member and the engagement member are connected through a pin.

In some embodiments, the conjugate 11 is assembled by a pin. As shown in FIG. 8, a pinhole is provided at each end of the first engagement member 1, the second engagement member 3, the first resilient member 2 and the second resilient member 4. The ends of the first engagement member 1, the second engagement member 3, the first resilient member 2 and the second resilient member 4 are fixedly connected through inserting the pin 8 into the pinholes. The endoscopic clip is easily detachable through pulling out the pin 8 from the pinholes.

Figure 9:
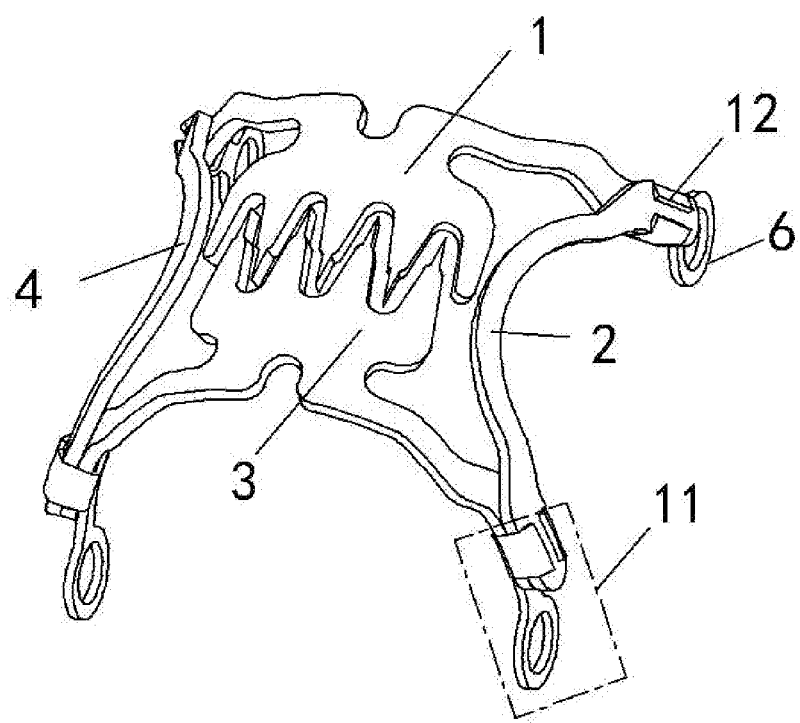
FIG. 9 is a schematic diagram of the endoscopic clip according to an embodiment of the present application, in which the resilient member and the engagement member are connected through a clamp.

In some embodiments, the conjugate 11 is assembled by a clamp 12. As shown in FIG. 9, a clamping slot is provided at each end of the first engagement member 1, the second engagement member 3, the first resilient member 2 and the second resilient member 4. The ends of the first engagement member 1, the second engagement member 3, the first resilient member 2 and the second resilient member 4 are fixedly connected through the engagement of the clamping slot and the clamp 12. The endoscopic clip is easily detachable through removing the clamp 12.

Figure 10:
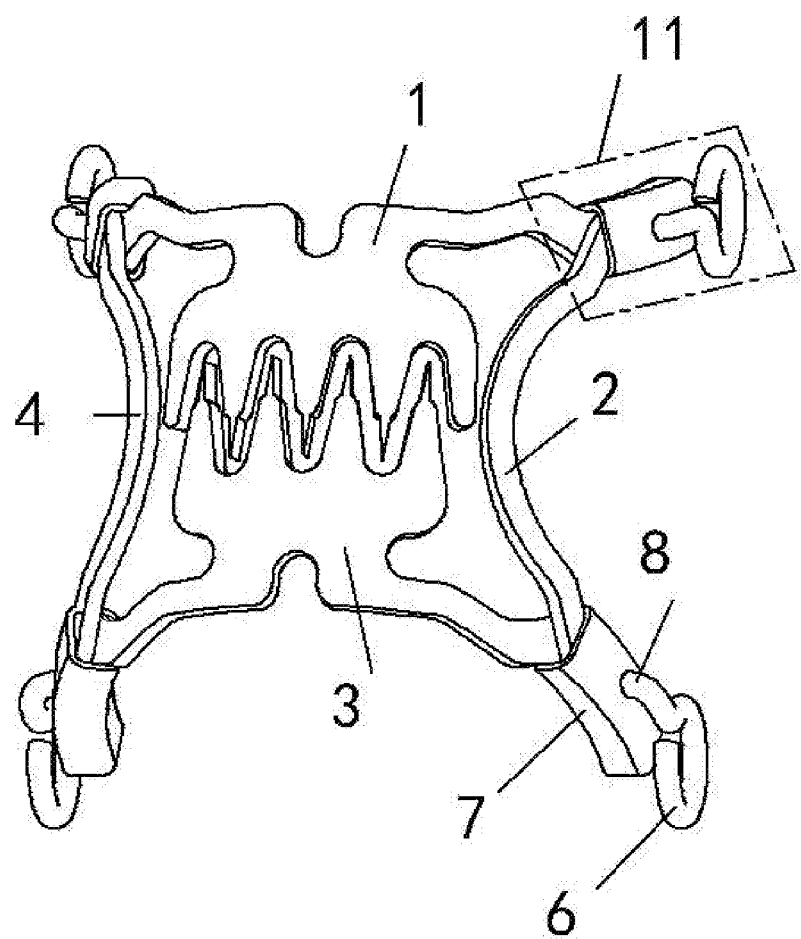
FIG. 10 is a schematic diagram of the endoscopic clip according to an embodiment of the present application, in which the resilient member and the engagement member are connected through both the pin and the tube.

In some embodiments, the conjugate 11 is assembled by both the tube and the pin. As shown in FIG. 10, a through hole corresponding to the pinhole is provided at the tube 7, and an end of the engagement member and an end of the resilient member are connectable through inserting the pin 8 into the through hole and the pinhole. The pin 8 not only strengthens the connection, but also prevents the tube 7 from falling off. The endoscopic clip is easily detachable through pulling out the pin 8 and removing the tube 7, so as to facilitate the removal of the endoscopic clip.

Figure 11:
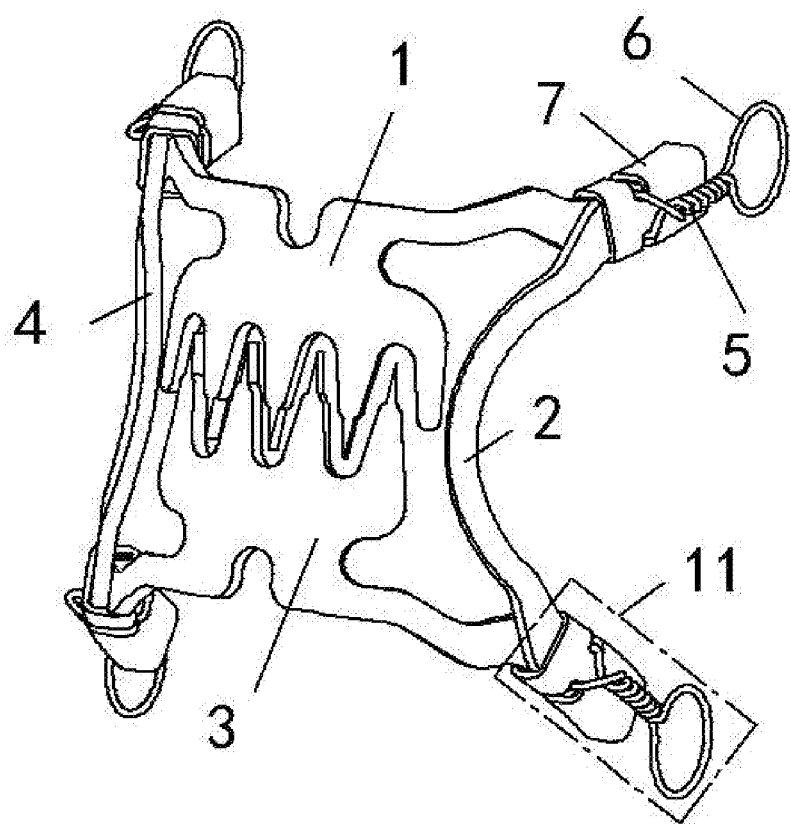
FIG. 11 is a schematic diagram of the endoscopic clip according to an embodiment of the present application, in which the resilient member and the engagement member are connected through both the tube and the binding wire.

In some embodiments, the conjugate 11 is assembled by both the tube and the binding wire. As shown in FIG. 11, openings are provided at two sides of the tube 7; the openings are aligned with limit grooves; and a binding wire 5 is wound in the opening and the limit groove. The binding wire 5 is preferably made of metal, and is wound or tied for the binding. The endoscopic clip is detachable through untying the binding wire 5 and removing the tube 7.

It should be noted that the endoscopic clip is assembled through detachable elements, such as binding wires, tubes, pins and clamps, and these assembling ways are applicable to all embodiments of the present application and will not be further illustrated in other embodiments. In addition, other detachable assembling ways should also fall in the protection scope of the present application.

Embodiment 2

A second embodiment of an endoscopic clip of the present application is shown in FIGS. 12-17. Compared with the first embodiment, in this embodiment, an end of the first engagement member is fixedly connected with an end of the first resilient member, and/or the end of the second engagement member is fixedly connected with an end of the second resilient member.

Figure 12:
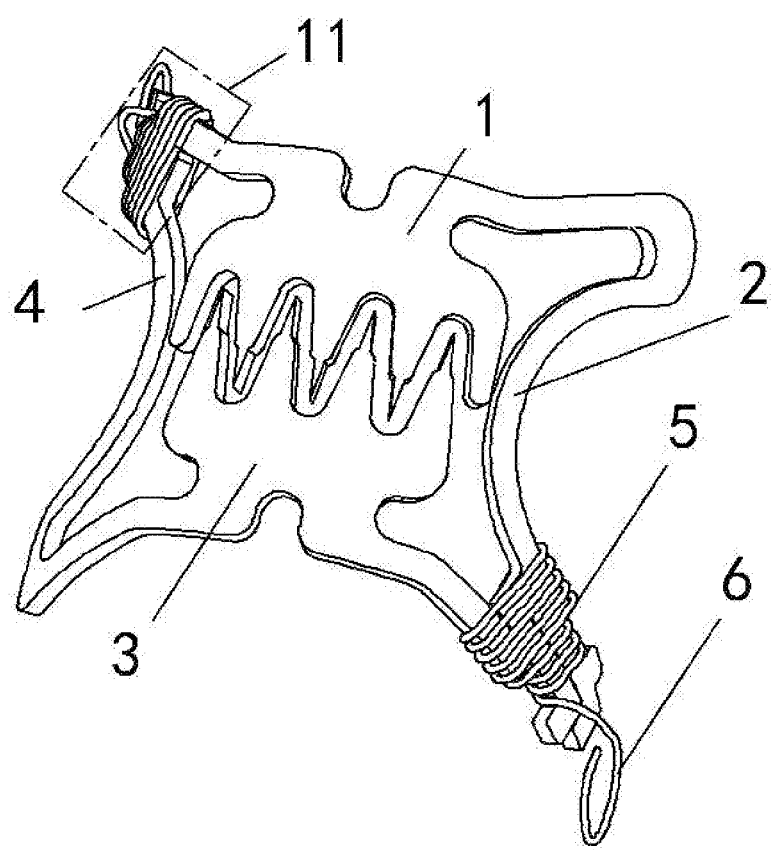
FIG. 12 is a schematic diagram of an endoscopic clip according to a second embodiment of the present application, in which the conjugates diagonally opposite to each other are detachable.
Figure 13:
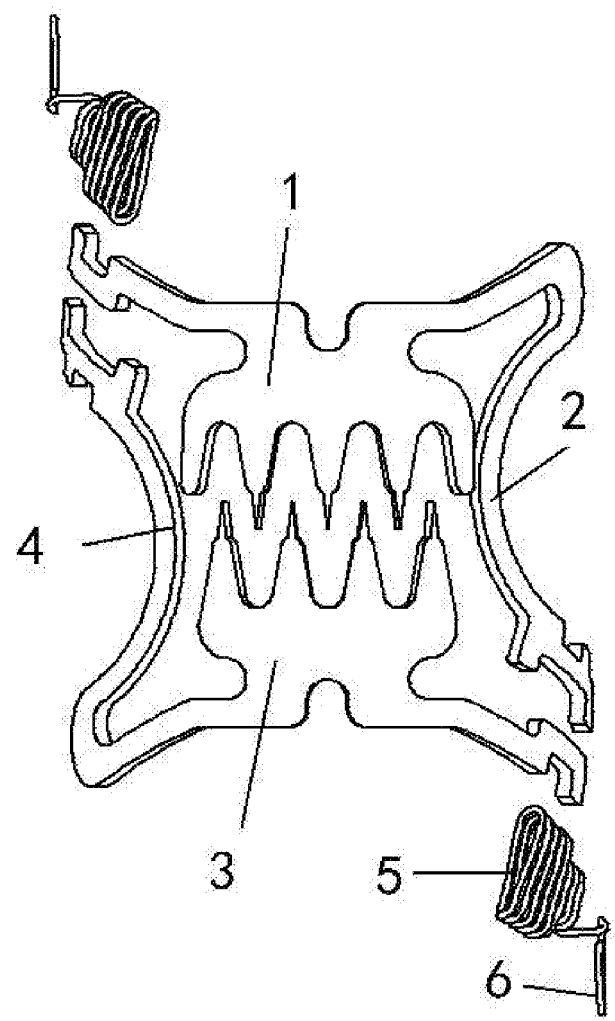
FIG. 13 is a schematic diagram of the endoscopic clip in FIG. 12, in which the endoscopic clip is detached.

As shown in FIGS. 12-13, the endoscopic clip includes a first engagement member 1, a first resilient member 2, a second engagement member 3, and a second resilient member 4. The first engagement member 1 and the second engagement member 3 are both provided with teeth and protrusions. The first engagement member 1 and a first resilient member 2 are fixedly connected to form an independent structure, whereas a second engagement member 3 and a second resilient member 4 are fixedly connected to form another dependent structure, and the two independent structures are connected to form the endoscopic clip with two diagonally opposite conjugates 11.

Figure 14:
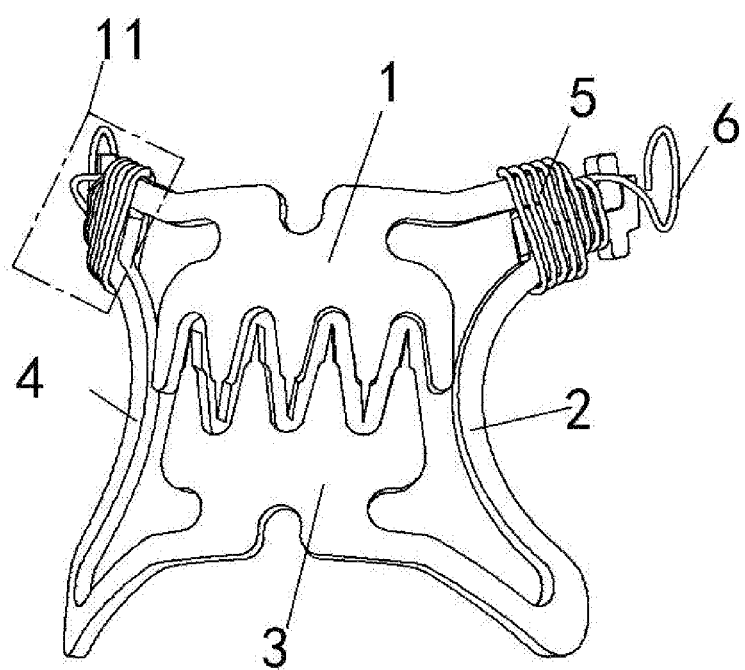
FIG. 14 is a schematic diagram of the endoscopic clip according to the second embodiment of the present application, in which the conjugates adjacent to each other are detachable.
Figure 15:
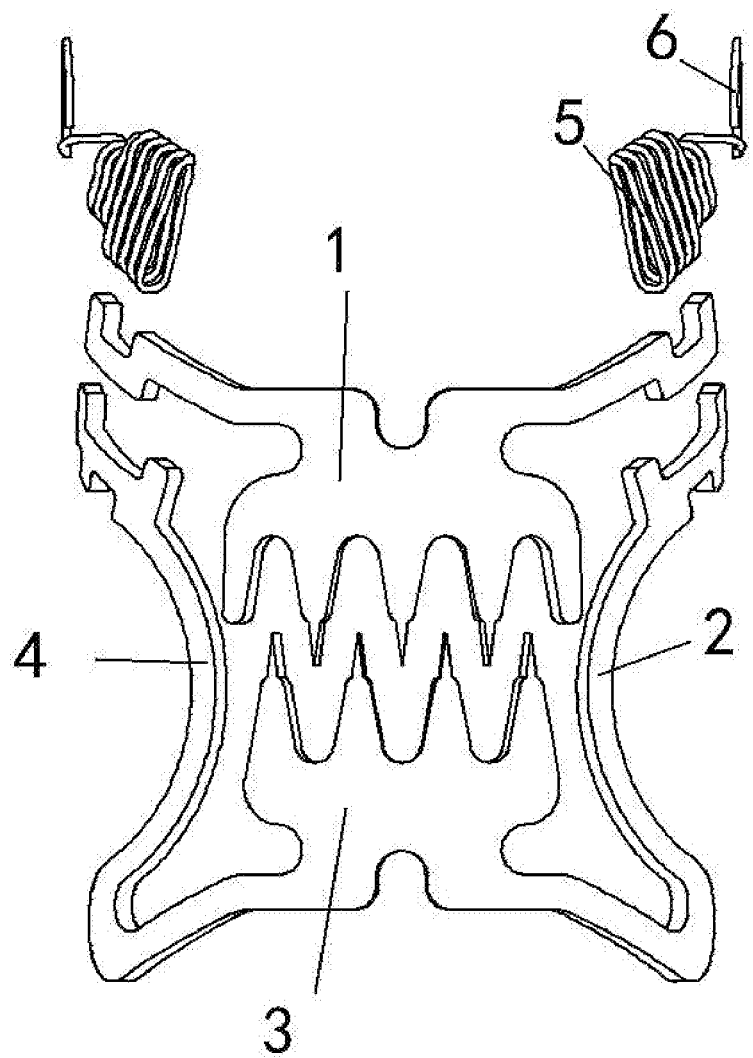
FIG. 15 is a schematic diagram of the endoscopic clip in FIG. 14, in which the endoscopic clip is detached.

As shown in FIGS. 14-15, two ends of a second engagement member 3 are fixedly connected with an end of a first resilient member 2 and an end of a second resilient member 4 respectively to form an independent structure, and the independent structure and a first engagement member 1 are connected to form the endoscopic clip with two adjacent detachable conjugates 11.

Figure 16:
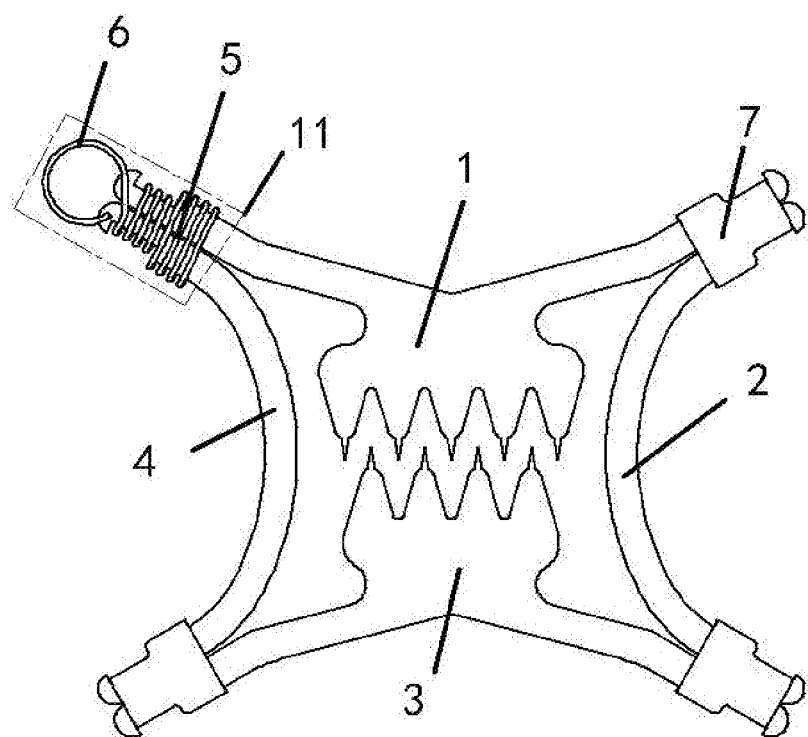
FIG. 16 is a schematic diagram of the endoscopic clip of the second embodiment of the present application, in which one conjugate is detachable.
Figure 17:
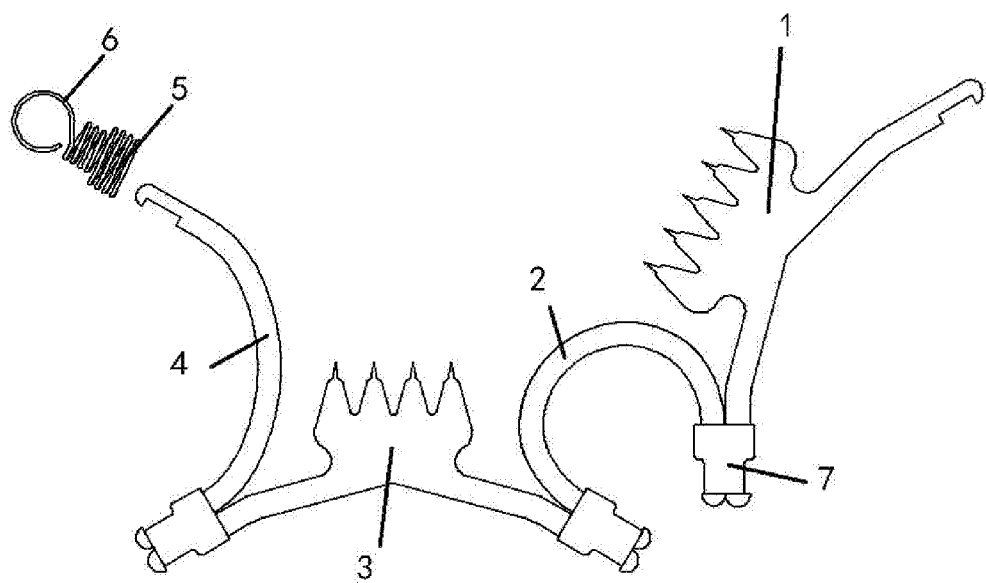
FIG. 17 is a schematic diagram of the endoscopic clip in FIG. 16, in which the endoscopic clip is detached.

As shown in FIGS. 16-17, two ends of a first resilient member 2 are fixedly connected with an end of a first engagement member 1 and an end of a second engagement member 3 respectively; an end of the second resilient member 4 is fixedly connected with the other end of the second engagement member 3; and the other end of the second resilient member 4 is connectable with the other end of the first engagement member in a detachable manner, such as binding connection. A curvity of the first resilient member 2 is larger than that of the second resilient member 4 to allow the endoscopic clip to be detached more easily. When assembled, the endoscopic clip is of a plane structure with four corners. When the endoscopic clip is detached, the first resilient member 2 and the second resilient member 4 are deformed, and due to the difference in curvity, a recurrent force of the first resilient member 2 is larger than that of the second resilient member 4. During the detachment of the endoscopic clip, a binding wire 5 is untied at first, and then the first engagement member 1 and the second engagement member 3 are opened under the larger recurrent force of the first resilient member 2. The endoscopic clip in this embodiment can be more easily detached with less operations owing to the larger recurrent force of the second resilient member 2.

Embodiment 3

Figure 18:
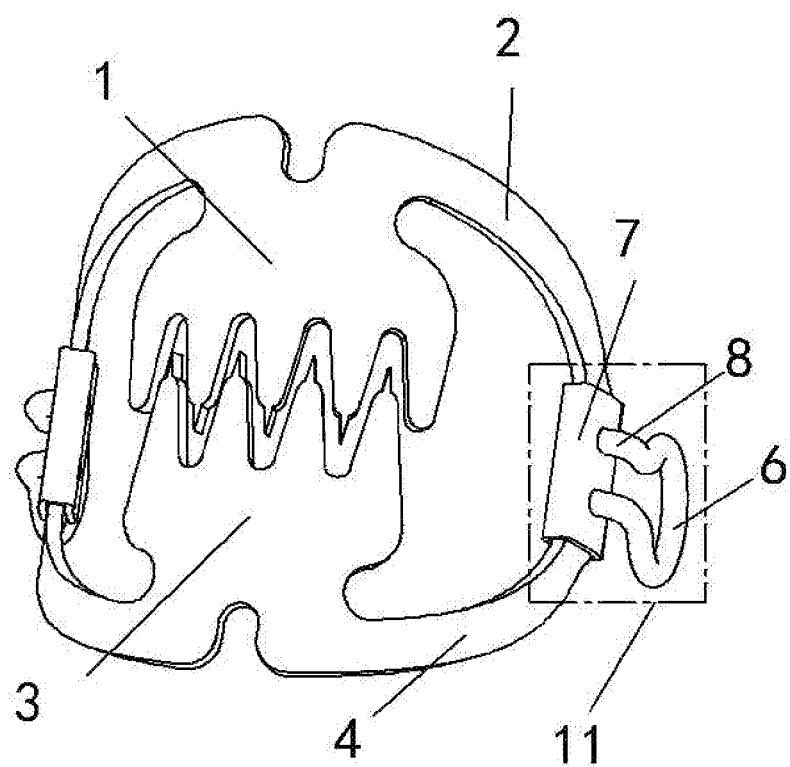
FIG. 18 is a schematic diagram of an endoscopic clip according to a third embodiment of the present application.
Figure 19:
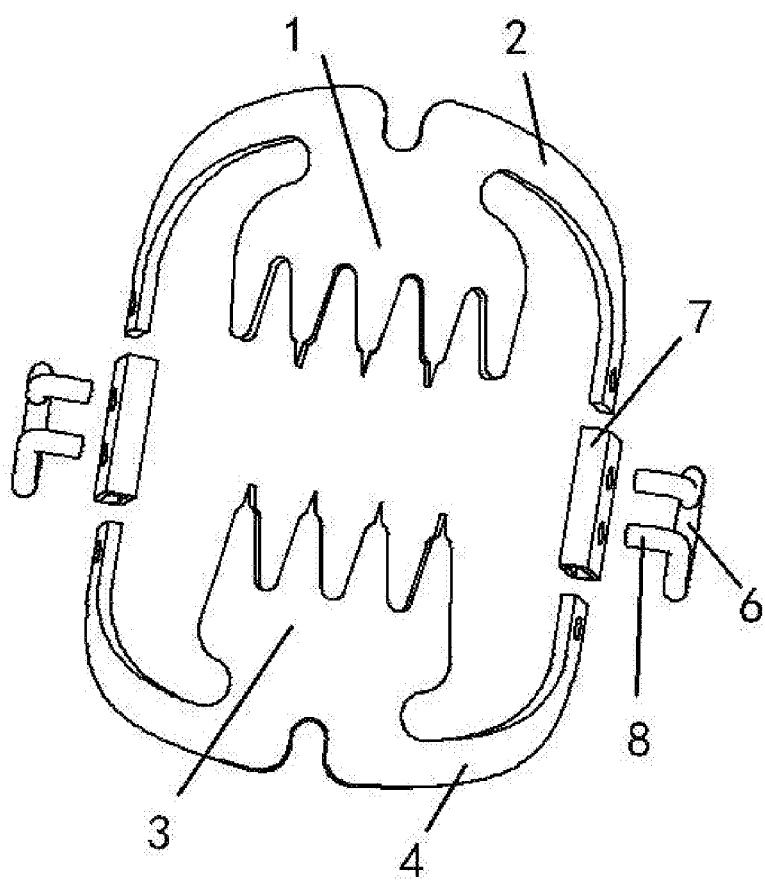
FIG. 19 is a schematic diagram of the detached endoscopic clip in FIG. 18, in which the endoscopic clip is detached.

A third embodiment of an endoscopic clip of the present application is shown in FIGS. 18-19. A conjugate 11 is assembled by both the tube and the pin. The engagement member is made of metal with resilience. The protrusions of the first engagement member 1 and the second engagement member 3 which are resilient are used as the resilient members. and have arc structures bent towards the engagement structure formed by the first engagement member and the second engagement member when the endoscopic clip is assembled. A pinhole is provided at each end of the protrusions of the first engagement member 1 and the second engagement member 3, and through holes corresponding to the pinholes are provided at the tube 7. An end of the protrusions of the first engagement member 1 and an end of the second engagement member 3 are connectable through inserting a pin 8 into the pinhole to form two conjugates 11 that are symmetrically arranged at the middle portion of the endoscopic clip. The conjugate 11 of this embodiment includes the end the protrusion of the first engagement member 1, the end of the protrusion of the second engagement member 3, the tube 7 and the pin 8. To assemble the endoscopic clip, the end of the protrusion of the first engagement member 1 and the end of the end of the protrusion of the second engagement member 3 are inserted into the tube 7, and then the pin is inserted into the pinhole and the through hole. To detach the endoscopic clip, the pin 8 is pulled out at first, and then the end of protrusion of the first engagement member 1 and the end of the end of the protrusion of the second engagement member 3 are pulled out from the tube 7. When assembled, the endoscopic clip of this embodiment is of an arch structure.

In this embodiment, the tube 7 is preferably made of metal, and the pin 8 is preferably made of metal. The metal tubular portion 7 and the metal pin 8 can strengthen the clipping stability of the endoscopic clip and extend the service life of the endoscopic clip.

In this embodiment, the conjugate 11 may be assembly by the tube only. A limit groove is provided at the end of the resilient member, and a limit part engaged with the limit groove is provided at the tube 7. The conjugate 11 herein, with few members, is simple and convenient to be assembled and detached, and the members of the conjugate 11 are less likely to be lost.

In this embodiment, at least one pinhole and at least one through hole are provided. The number of the pinhole and the through hole is designed according to actual situations, and the number of the pin matches that of the pinhole and the through hole.

In order to improve the clipping performance of the endoscopic clip, the protrusions of the first engagement member 1 and the second engagement member 3 are preferably made of nickel-titanium shape-memory alloy, which can provide the endoscopic clip with a continuously stable clipping force, so that the endoscopic clip can give a better clipping performance.

In order to easily remove the endoscopic clip, a circular pulling portion is provided at the end of the pin that is not inserted into the pinhole.

Embodiment 4

Figure 20:
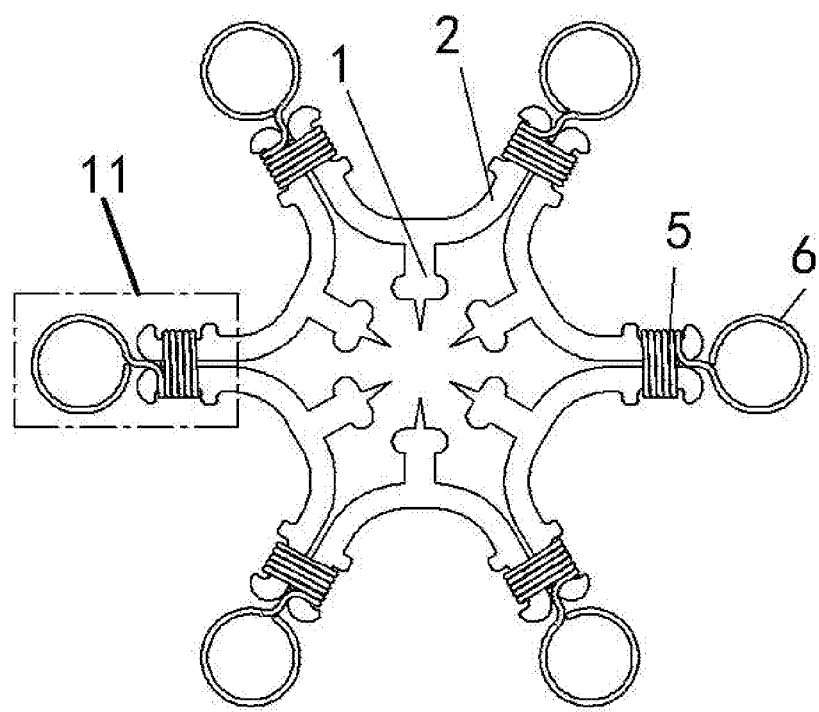
FIG. 20 is a schematic diagram of an endoscopic clip according to a fourth embodiment of the present application.
Figure 21:
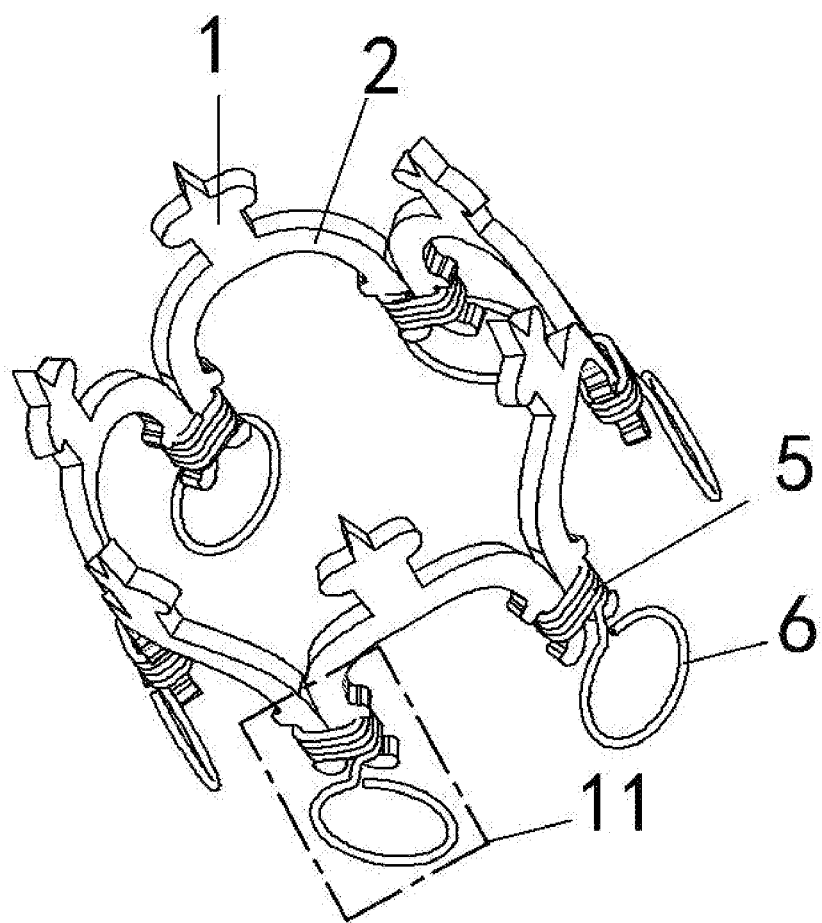
FIG. 21 is a schematic diagram of the endoscopic clip in FIG. 20 in an open state.

A fourth embodiment of an endoscopic clip of the present application is shown in FIGS. 20-21. The endoscopic clip herein includes six engagement members that are centrally symmetric. The engagement member 1 and the resilient member 2 are formed integrally. The engagement member 1 includes teeth and two protrusions which are resilient, where the two resilient protrusions are used as the resilient member 1. The protrusions are of an arc structure that bends away from the teeth. The protrusions are connectable to form six conjugates 11. The conjugate is assembled through the binding wire 5. The endoscopic clip, when assembled, is of a flat hexagonal star structure. The endoscopic clip is assembled through assembling the conjugates 11 with binding wire, and the endoscopic clip is detachable through removing the binding wire.

Preferably, the engagement member is made of metal with resilience, and more preferably nickel-titanium shape-memory alloy, to provide the endoscopic clip with a continuously stable clipping force and a good clipping performance.

Preferably, the binding wire 5 is made of metal, such as stainless steel, to achieve a good fastening performance.

An end of the binding wire 5 is fixed connected with the protrusion of the engagement member, and the other end of the binding wire 5 is provided with a circular pulling portion 6 to quickly detach and remove the endoscopic clip.

In this embodiment, at least three engagement members are provided. The number of the engagement member is selected in other embodiments according to actual situations.

Figure 22:
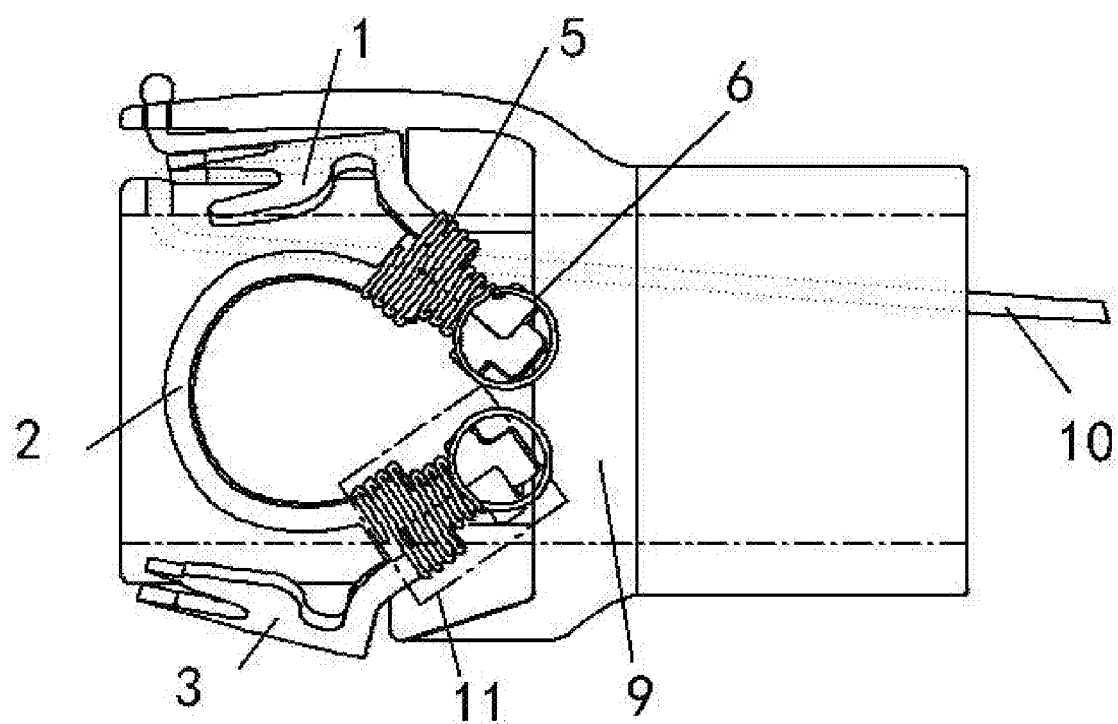
FIG. 22 schematically shows the mounting and releasing of the endoscopic clip in FIG. 1.

FIG. 22 schematically shows the mounting and releasing of the endoscopic clip in FIG. 1. In order to mount the endoscopic clip, the first resilient member 2 and the second resilient member 4 are bent to deform, which drives the first engagement member 1 and the second engagement member 3 to turn the teeth thereof outwardly. At last, the endoscopic clip is mounted outside a transparent cap arranged at an end of the endoscope, such that the first engagement member 1 and the second engagement member 3 are in an open state, and the sharp portions on the teeth point toward an end of the transparent cap 9 away from the endoscope. A pulling wire 10 is pulled to drive the endoscopic clip to move towards the end of the transparent cap 9 away from the endoscopic and then separate with the transparent cap, so as to release the endoscopic clip. At the releasing moment, the first resilient member 2 and the second resilient member 4 quickly return to their original shapes, which drives the teeth of the first engagement member 1 and the second engagement member to turn inwardly and clip the tissue tightly to realize the closure of the tissue. When the clipped tissue has healed, the detaching member passes through a channel of the endoscope and catches the circular pulling portion to unfasten the binding wire 5 in a reverse winding direction of the binding wire 5. The endoscopic clip is detached before being removed, so the removal of the endoscopic clip becomes easier. Notably, the releasing method of the endoscopic clip of this embodiment is applicable for all embodiments of the present application.

The embodiments disclosed herein are only preferred embodiments and not limited to the scope of the present application. Any change, modification and replacement made by those skilled in the art without departing from the spirit of the invention should fall within the scope of the invention.

What is claimed is:

1. A detachable endoscopic clip for anastomosis, comprising:
   at least one detachable connector, the detachable connector being a binding wire, a tube, a pin, a clamp, or a combination thereof;
   at least two engagement members; and
   at least two resilient members;
   wherein terminal ends of the at least two engagement members are respectively connected to terminal ends of the at least two resilient members to form a plurality of conjugates;
   at least one of the conjugates is detachable through the detachable connector;

a limit portion is provided at an end of at least one of the at least two engagement members and an end of at least one of the at least two resilient members, respectively, and configured to engage with the detachable connector;

a pulling portion is provided at the detachable connector, and configured for detaching the detachable endoscopic clip in a patient's body; and the detachable endoscopic clip is detached by detaching at least one of the conjugates.

2. The detachable endoscopic clip of claim 1, wherein the at least two engagement members comprise a first engagement member and a second engagement member; and the at least two resilient members comprise a first resilient member and a second resilient member;

ends of the first engagement member, ends of the first resilient member, ends of the second engagement member, and ends of the second resilient member are connected to form the plurality of conjugates; the first engagement member and the second engagement member engage with each other when at least one of the plurality of conjugates is assembled by the detachable connector; and the first engagement member and the second engagement member are separated from each other when the detachable connector is detached.

3. The detachable endoscopic clip of claim 2, wherein two of the plurality of conjugates diagonally opposite to each other are detachable.

4. The detachable endoscopic clip of claim 3, wherein the at least two resilient members are made of metal.

5. The detachable endoscopic clip of claim 2, wherein two adjacent conjugates of the plurality of conjugates are detachable.

6. The detachable endoscopic clip of claim 5, wherein the at least two resilient members are made of metal.

7. The detachable endoscopic clip of claim 2, wherein the at least two resilient members are made of metal.

8. The detachable endoscopic clip of claim 1, wherein at least one of the at least two engagement members and at least one of the at least two resilient members are integrally formed; each of the at least two resilient members is a resilient protrusion and is arranged at both sides of each of the at least two engagement members; and each of the at least two engagement members is provided with teeth.

9. The detachable endoscopic clip of claim 8, wherein the at least two resilient members are made of metal.

10. The detachable endoscopic clip of claim 1, wherein the at least two resilient members are made of metal.

* * * * *